United States Patent [19]

Bittings

[11] 4,358,539
[45] Nov. 9, 1982

[54] THROW-AWAY SUBCULTURING DEVICE

[75] Inventor: Gilbert S. Bittings, Baltimore, Md.

[73] Assignee: Becton, Dickinson and Company, Paramus, N.J.

[21] Appl. No.: 245,785

[22] Filed: Mar. 20, 1981

[51] Int. Cl.³ .......................... C12M 1/20; C12Q 1/24
[52] U.S. Cl. ................................. 435/301; 128/272.3;
   435/292; 435/293; 435/294; 435/296; 435/297;
   435/298; 435/299; 435/300; 435/30; 435/810
[58] Field of Search .................... 128/272.3; 435/292,
   435/293, 294, 296, 297, 298, 299, 300, 301, 810,
   30

[56] References Cited

U.S. PATENT DOCUMENTS

| | | | |
|---|---|---|---|
| 2,992,974 | 7/1961 | Belcone et al. | 435/299 |
| 3,893,892 | 7/1975 | Mehl | 435/30 X |
| 4,116,066 | 9/1978 | Mehl et al. | 73/421 R |
| 4,308,347 | 12/1981 | Forrer et al. | 435/300 X |

OTHER PUBLICATIONS

Pfizer Advertisement for Airway Needle/Subculture Unit.

*Primary Examiner*—Robert J. Warden

[57] ABSTRACT

A device is provided for blind subculturing in place of a standard petri dish, which device eliminates the need for a separate needle and syringe. The device includes a culture media in combination with an absorbent fiber disc adjacent the culture media for absorbing inoculum and maintaining it adjacent the media gel. In addition, a mounted needle is included in the device for penetrating the septum of a standard culture bottle, for withdrawing the inoculum. Means are provided for readily removing the culture media from the device momentarily for inspection, with the means including a cooperating closure assembly on the device utilizing a conventional petri plate as the top and/or bottom cap or closure.

9 Claims, 1 Drawing Figure

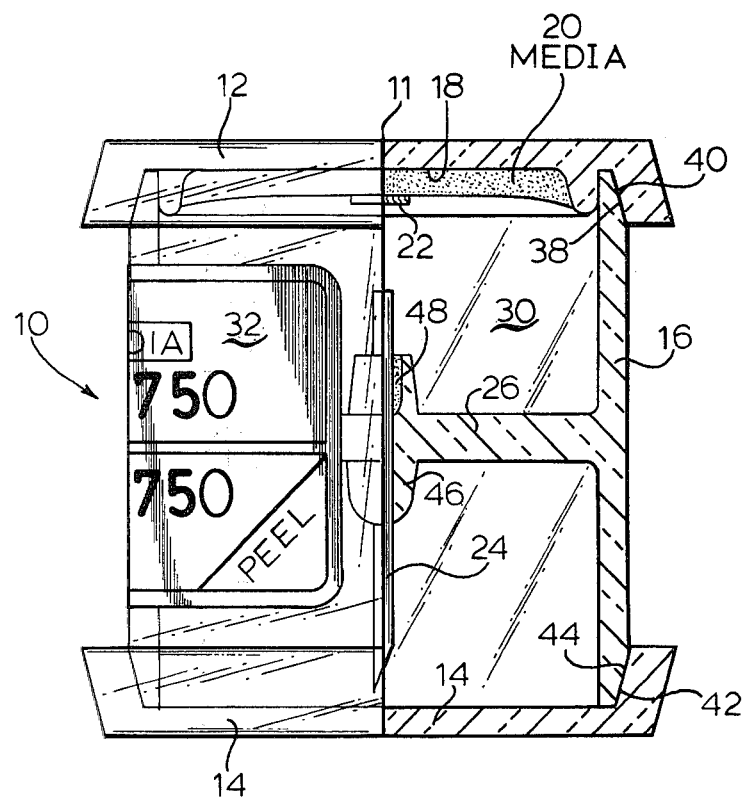

THROW-AWAY SUBCULTURING DEVICE

BACKGROUND AND STATEMENT OF THE INVENTION

This invention relates to a device for subculturing inoculum from a standard culture bottle, with the device being utilized generally as a substitute for individual petri dishes or plates. The device includes an arrangement which supports a media gel, such as agar, for culturing the inoculum withdrawn from a standard culture bottle, together with an absorbent fiber disc mounted on the media gel so that the disc will absorb the inoculum and maintain a substantial measured portion of the inoculum adjacent the culture media for the culturing procedure. In addition, the device includes a needle mounted in fixed fashion in the device for penetrating the septum of a standard culture bottle for withdrawing the inoculum for the blind subculturing procedure.

The arrangement is such as to eliminate the use of the usual separate needle and syringe for withdrawing the inoculum from the standard culture bottle, and placing it on a standard petri plate or dish for the subculture procedure. By having an automatic procedure wherein the mounted needle of the device is inserted in the septum of the culture bottle, the culture bottle inverted together with the device of the invention, the disc on the media surface is saturated with inoculum in the desired quantity. With further inverting of the bottle and subculture device of the invention, the subculture device can then be removed from the upright culture bottle without any further activity and without the need for separate materials and arrangements for this transfer procedure.

By eliminating the need for a separate syringe and needle, of course, the problem of contamination is reduced substantially. That is, as will be appreciated by practitioners-in-the-art, the use of a separate syringe and needle for penetrating the septum of a standard culture bottle and placing an inoculum sample on a media gel, and subsequently closing the plate containing the media gel, there is a much greater opportunity for contamination of the subculture being reviewed.

As a further feature of the invention, the device may be maintained on the culture bottle in a manner wherein once the standard culture bottle and device have been inverted and then re-inverted, the standard culture bottle with the device and its needle inserted therein may be replaced into the incubator without removal of the device, in accordance herewith from the standard culture bottle. In this respect, the device of the invention includes a removable cap containing the culturing media and the saturated disc containing the absorbed inoculum. The cap may be momentarily removed for inspection, as required. The latter procedure would be utilized, generally, as will be understood by practitioners-in-the-art, if a terminal subculture procedure is being carried out. For an intermediate subculture, the device of the invention would be removed from the bottle, capped and incubated separately. For this reason, the invention includes a peel-off numbered label for marking the bottle so as to maintain a connection between the device of the invention which has been removed from the standard culture bottle, and the bottle itself.

In accordance with a further feature of the invention the removable cap may be a conventional petri plate or dish. The device of the invention is configured adjacent the top and bottom so as to receive a conventional petri dish as the cap therefor, if desired.

Preferably, the device will be comprised of a transparent material so that the contents may be observed. Preferably, the material will be a transparent resin, and may be, for example, a polystyrene, a polycarbonate or methyl methacrylate. The culture media will be selected, as will be understood, depending upon the culturing that is being carried out. An agar gel is representative of one culture media which may be utilized. The absorbent disc on the culture media for absorbing the inoculum may be comprised of, for example, an inert paper fiber. Its dimensions will be selected so as to maintain a predictable amount of inoculum intimate with the gel surface for incubation. As will be appreciated, the device is a throw-away device and is comprised of materials which are inexpensive for this purpose. In addition, the simplicity of arrangement is such that the device may be manufactured by mass production techniques making it commercially attractive.

Other objects and advantages of this invention will now be described in the following detailed description the accompanying drawing, and the appended claims.

DESCRIPTION OF THE DRAWING

The single FIGURE is a view in elevation and partially in section showing an embodiment of a device illustrating the invention.

DETAILED DESCRIPTION OF THE INVENTION

Referring to the drawing, the invention is illustrated for use as a transparent throw-away device 10, tubular in shape, with an annular vertical wall 16 ending at the top in an annular surface 38, and at the bottom in an annular surface 44, with surfaces 38 and 44 converging toward the axis 11 of device 10. A top cap 12 is received on the top of wall 16 and is press fit into place with top cap 12 having a downwardly diverging annular surface 40 for cooperating with surface 38. Similarly, bottom cap 14 has an upwardly diverging surface 42 for cooperating with surface 44 for a press-fit engagement onto the bottom of annular wall 16. A representative angle from axis 11 of surfaces 38 and 44 which may be used is between about 3 and 5 degrees. In this connection, it is within the purview of this invention that top cap 12 and/or bottom cap 14 may be a conventional petri plate. Of course, other configurations may be used for a cooperating connection between the caps and annular wall 16, as will be appreciated, including for example, a cooperating annular abutment and groove configuration.

Integral with wall 16 is a circular web 26 positioned substantially centrally in the cavity 30 of device 10. Web 26 serves as a support for needle 24 with web 26 including an integral vertical support portion 46 for holding needle 28 erect, and including a seal 48.

As is shown in the drawing, cap 12 includes internally thereof a well 18 for receiving a culture media 20 therein such as agar. Positioned centrally of the culture media deposited in well 18 is an absorbent disc 22 for absorbing and maintaining the inoculum adjacent media 20. As mentioned above, the device may include a peel-off label 32 for use in identifying the subculture media in the device 10 relative to a culture bottle from which the inoculum contained therein was withdrawn.

While the device 10 may be of any size and/or configuration, as will be appreciated, a representative size dimension for a subculture medium device which may be thrown away after use and which is a substitute for a conventional petri plate will have a height of about 1.6 inches and a diameter of about 1.50 inches. With these dimensions, needle 24 will be about one inch in length. As discussed above, it is preferable that at least top cap 12 and annular walls 16 be comprised of a transparent material and one which is semi-rigid in order to accommodate the press-fitting of cap 12 and cap 14. As will be appreciated, cap 14 is a protective cap utilized to protect and maintain the sterile environment of needle 24 until such time as the device 10 is to be used. Cap 12 may be as discussed above, a petri plate or dish, and may be removed from time to time during incubation to inspect the status of the subculture of media 20 and disc 22.

Thus, in a representative procedure, for using device 10, protective cap 14 is removed in order to expose needle 24. The needle 24 is then inserted into and penetrates through the septum of a culture bottle. Subsequent to this insertion, the bottle together with subculture device 10 is inverted to saturate disc 22 on the media 20 surface. Subsequently, the bottle and subculture device are again inverted. At this point in time, both the bottle and the device may be incubated together particularly if a terminal subculture procedure is being carried out. No separate labeling procedure is required under these circumstances since device 10 will remain connected to the conventional standard culture bottle.

Alternatively, if an intermediate subculture is being carried out, the device 10 may be removed from the standard culture bottle and the label 32 peeled off from device 10 and placed on the bottle in order to maintain an identification between the two. At this point, the protective cap 14 is replaced on the bottle and the subculture device 10 is incubated in its inverted position.

Thus, as will be appreciated from the above, a convenient throw-away inexpensive device is provided, in accordance herewith, for carrying out subculturing from a standard culture bottle with the device being utilized in place of a standard petri dish, and with the device eliminating the need for a separate syringe and needle. The transferring procedure from the standard culture bottle to the device of the invention is carried out with a minimum of handling, thus reducing contamination. Moreover, the absorptive disc utilized in accordance with the device of the invention is constructed to absorb and maintain a desired predictable amount of the inoculum being examined adjacent the gel surface for carrying out the incubation procedure. As will be appreciated, further, since the device is a throw-away device comprised of a relatively inexpensive plastic material it may be mass produced conveniently and inexpensively.

While the forms of apparatus herein described constitute a preferred embodiment of the invention, it is to be understood that the invention is not limited to this precise form of apparatus and that changes can be made therein without departing from the scope of the invention which is defined in the appended claims. For example, the device may be enlarged and compartmented into segregated half or quarter-sections with separate culture mediums and needles so that two, three or four separate subcultures may be carried out simultaneously. In this connection, the device may be conveniently square or rectangular in cross section, as will be understood.

What is claimed is:

1. A throw-away subculture device, characterized by
   (a) a container defining an enclosure with a top opening and a bottom opening;
   (b) a top cap for said top opening;
   (c) a bottom cap for said bottom opening;
   (d) a web spaced from said top cap dividing said enclosure into two chambers one of which defines a subculture area in said enclosure;
   (e) at least one well and culture media in said top cap for cooperation with said subculture area;
   (f) at least one absorbent fiber disc mounted adjacent said well for receiving inoculum introduced into said subculture area; and
   (g) at least one needle mounted in said web and extending therethrough for introducing inoculum to said subculture area, the point of said needle extending toward said bottom cap.

2. The apparatus of claim 1, further characterized by
   (a) said container is tubular;
   (b) cooperating angular surfaces between said container and said top cap;
   (c) cooperating angular surfaces between said container and said bottom cap; and
   (d) whereby said top cap and said bottom cap are press-fit onto said container.

3. The apparatus of claim 1, further characterized by
   (a) said absorbent fiber disc is comprised of an inert paper fiber.

4. The apparatus of claim 3, further characterized by
   (a) said disc is of a size to maintain a pre-determined quantity of incoulum adjacent said culture media during culturing.

5. The apparatus of claim 1, further characterized by:
   (a) said container, said top cap and said bottom cap are comprised of a transparent plastic.

6. The apparatus of claim 1, further characterized by:
   (a) a peelable label for identifying said device and its associated culture bottle.

7. A throw-away subculture device characterized by:
   (a) a tubular container open at the top and the bottom, said container comprised of a semi-rigid material;
   (b) a top cap for said container;
   (c) a bottom cap for said container;
   (d) cooperating angular surfaces between said container and said top and bottom caps;
   (e) a well in said top cap defining a media container for said device;
   (f) a web integral with said tubular container walls and mounted spaced from said top opening dividing said container into two chambers one of which defines a subculture area in said container;
   (g) an absorbent fiber disc in said subculture area for receiving inoculum introduced into said subculture area; and
   (h) a needle supported in said web and extending therethrough, with the point thereof extending toward said bottom opening.

8. The apparatus of claim 7, further characterized by:
   (a) said absorbent fiber disc is comprised of an inert paper fiber.

9. The apparatus of claim 8, further characterized by:
   (a) said disc is of a size to maintain a pre-determined quantity of inoculum adjacent said culture media during culturing.

* * * * *